United States Patent [19]

Holtkamp

[11] Plant 4,975

[45] Jan. 18, 1983

[54] AFRICAN VIOLET PLANT

[76] Inventor: Reinhold Holtkamp, Werther Strasse 112, D-4294 Isselburg, Fed. Rep. of Germany

[21] Appl. No.: 165,075

[22] Filed: Jul. 1, 1980

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African Violet plant known by the cultivar name Oklahoma and particularly characterized by its large non-dropping flowers with frilled edges, generally purplish-red flower color, with certain petals being lighter in color than others, upright flower stems, vigorous and compact growth habit, and by its floriferousness, with up to 15 flowers being carried on each stem.

1 Drawing Figure

1

The present invention comprises a new and distinct cultivar of African Violet plant, botanically known as *Saintpaulia ionantha,* and hereinafter referred to by the cultivar name Oklahoma. Oklahoma is a product of a planned breeding program and was identified during the breeding and selection process by the designations E 61/2 and 188/79.

The new cultivar was originated from a cross made in a controlled breeding program in Isselburg, Rhineland, Germany. The female, or seed parent was known for breeding purposes by the designation b. 15/12, a red single cultivar having upright flower stems and a compact, rich flower head. The female parent is not patented. The male, or pollen parent was known for breeding purposes by the designation 63/75, and thereafter by the cultivar name Colorado, disclosed and claimed in my U.S. Plant Pat. No. 4,266, granted June 20, 1978.

The new cultivar Oklahoma was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Oklahoma which in combination distinguish this African Violet as a new and distinct cultivar:

(1) Large flowers with frilled edges, with the flowers being non-dropping.

(2) Purplish-red flower color, with the three lower petals being relatively lighter in color than the upper two petals.

(3) Upright flower stem.

(4) Very floriferous, with up to 6–15 flowers per stem.

(5) Vigorous grower, saleable with first flash of flowers.

2

(6) Compact habit, with bouquet positioned centrally above leaves on rigid stems, thereby providing a pleasant contrast with the leaves.

The accompanying photographic drawing shows a typical specimen plant of the new cultivar. The colors appearing in the photograph are as true as possible with color illustrations of this type.

Oklahoma is similar in most respects to its male parent Colorado. Oklahoma is particularly distinguished from Colorado by its three larger, lower petals being relatively lighter in color than its two upper petals.

In the following description, color references are made to the Horticultural Color Chart issued by Wilson Colour Ltd., except where general color terms of ordinary significance are obvious.

Botanical classification: *Saintpaulia ionantha,* Ramat. cv Oklahoma.

Parentage:

*Male parent.*—63/75 (Colorado).

*Female parent.*—15/12.

Propagation: The new cultivar holds its distinguishing characteristics through successive propagations by leaf cuttings and by division of shoots.

Plant: From 8 cm. to 12 cm. tall when grown in pots, and approximately 20–25 cm. in diameter when fully grown.

Leaves:

*General form.*—Round to oval.

*Diameter.*—Up to 75 mm.

*Texture.*—Soft, hairy.

*Aspect.*—Velvety.

*Veins.*—Upperside, visible; underside, well pronounced and shiny.

*Color (upperside).*—HCC spinach green 0960.

*Color (underside).*—HCC green 000 658, partly reddish between veins.

*Petiole.*—Brownish green.

Flowers:

*Buds.*—Ball-shaped, 6–8 mm. before opening; dark brown-purple and hairy.

*Sepals.*—Color: Dark brown. Calyx: Flat, funnel shaped. Aspect: Spear-shaped. Peduncle: On young flowers dark brown; on older flowers greenish brown.

Individual flowers:

*Size.*—2 small petals 22 mm. long, and 3 large petals 25 mm. long.

*Color.*—Upperside: Two small petals, orchid purple 31; three large petals, orchid purple 31/2. Underside: Mallow purple 630/3.

*Borne.*—Flower stems have 5–15 flowers per stem; up to 10 flower stems with first flowering; flowers occasionally display an additional small petal in the center of the flower.

*Shape.*—All petals are frilled and wavy.

*Corolla.*—Up to 50 mm. in total diameter, with normally two small and three relatively larger petals having frilled edges.

*Flowering time.*—7–9 weeks to saleable plant with decorative flower heads having 8–12 flower stems, with continued budding.

Reproductive organs:

*Stamens.*—Two anthers, composed of 4 cells, with seed capsule pushed slightly through.

*Anthers color.*—Dresden yellow 64.

*Filaments.*—4–5 mm. long, light green-yellow with purplish edges.

*Styles.*—Purple, base of ovary light green, hairy.

*Pollen color.*—HCC Dresden yellow 64/3.

Roots: Normally developed.

Disease resistance: Good as experienced to date.

General Observations

Oklahoma is a very vigorous new cultivar, coming to flower approximately 6–8 weeks after potting, with the plant being in full flower in 10 weeks. The combined lighter and darker purple flower petals provide a very attractive flower, and with the above normal number of flower stems (up to 12 and more), the plant forms a heavy flower head of long lasting and non-dropping flowers.

I claim:

1. A new and distinct cultivar of African Violet plant, known by the cultivar name Oklahoma, as described and illustrated, and particularly characterized by its large non-dropping flowers with frilled edges, generally purplish-red flower color, with certain petals being lighter in color than others, upright flower stems, vigorous and compact growth habit, and by its floriferousness, with up to 15 flowers being carried on each stem.

* * * * *

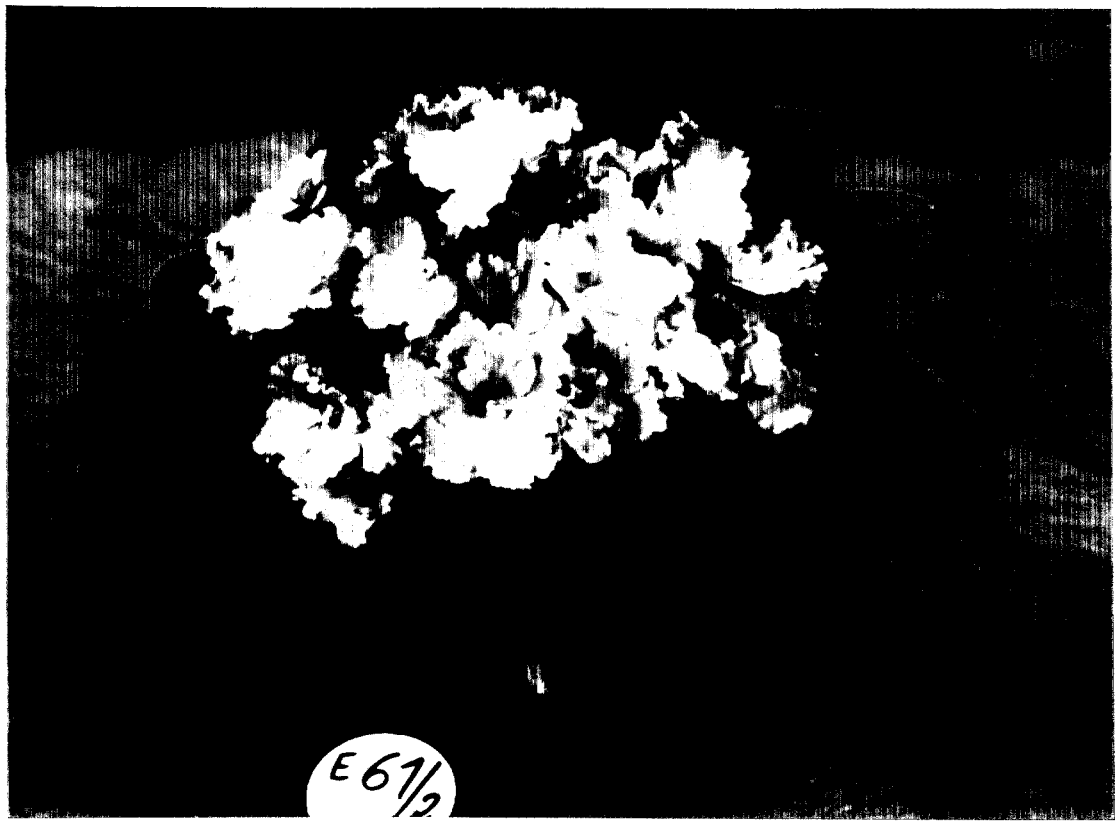
E 61/2